(12) United States Patent
Cheng et al.

(10) Patent No.: US 7,799,956 B2
(45) Date of Patent: Sep. 21, 2010

(54) PROCESS FOR PRODUCING PHENOL AND METHYL ETHYL KETONE

(75) Inventors: Jane Chi-ya Cheng, Bridgewater, NJ (US); John S. Buchanan, Lambertville, NJ (US); Doron Levin, Annandale, NJ (US); Michael A. Steckel, Bethlehem, PA (US); Jihad M. Dakka, Whitehouse Station, NJ (US); James P. Stokes, Katy, TX (US); John L. Robbins, Stockton, NJ (US); Jon E. Stanat, Baton Rouge, LA (US); Charles M. Smith, West University Place, TX (US); José G. Santiesteban, Hellertown, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 67 days.

(21) Appl. No.: 11/660,065

(22) PCT Filed: Aug. 5, 2005

(86) PCT No.: PCT/EP2005/008557

§ 371 (c)(1), (2), (4) Date: Feb. 12, 2007

(87) PCT Pub. No.: WO2006/015826

PCT Pub. Date: Feb. 16, 2006

(65) Prior Publication Data

US 2008/0086018 A1    Apr. 10, 2008

Related U.S. Application Data

(60) Provisional application No. 60/601,661, filed on Aug. 13, 2004.

(51) Int. Cl.
*C07C 45/00* (2006.01)
*C07C 37/08* (2006.01)

(52) U.S. Cl. ..................................... 568/385; 568/798

(58) Field of Classification Search .................. 568/385, 568/798; 585/446
See application file for complete search history.

(56) References Cited

U.S. PATENT DOCUMENTS

| | | | |
|---|---|---|---|
| 2,584,103 A | 2/1952 | Pines et al. | |
| 3,819,735 A | 6/1974 | Argento et al. | |
| 4,051,191 A | 9/1977 | Ward | |
| 4,490,565 A | 12/1984 | Chang et al. | |
| 4,490,566 A | 12/1984 | Chang et al. | |
| 4,891,458 A | 1/1990 | Innes et al. | |
| 4,992,606 A | 2/1991 | Kushnerick et al. | |
| 5,059,736 A | 10/1991 | Tamura et al. | |
| 5,177,283 A | 1/1993 | Ward | |
| 5,183,945 A | 2/1993 | Stibrany et al. | |
| 5,298,667 A | 3/1994 | Iwanaga et al. | |
| 5,336,820 A | 8/1994 | Owen et al. | |
| 5,371,310 A | 12/1994 | Bennett et al. | |
| 5,557,024 A | 9/1996 | Cheng et al. | |
| 5,922,920 A | 7/1999 | Bond et al. | |
| 6,002,057 A | 12/1999 | Hendriksen et al. | |
| 6,051,521 A | 4/2000 | Cheng et al. | |
| 6,169,215 B1 | 1/2001 | Levin et al. | |
| 6,169,216 B1 | 1/2001 | Levin et al. | |
| 6,297,406 B1 | 10/2001 | Levin et al. | |
| 6,410,804 B1 | 6/2002 | Levin et al. | |
| 6,440,886 B1 | 8/2002 | Gajda et al. | |
| 6,720,462 B2 * | 4/2004 | Duda et al. | ......... 568/768 |
| 2003/0083527 A1 | 5/2003 | Kuhnle et al. | |

FOREIGN PATENT DOCUMENTS

| | | |
|---|---|---|
| EP | 1 088 809 | 4/2001 |
| FR | 2 182 802 | 1/1974 |
| JP | 2002-282698 | 10/2002 |
| SU | 417405 | 2/1974 |
| SU | 265349 | 10/1976 |
| SU | 1245564 | 7/1986 |

OTHER PUBLICATIONS

"Alkylation of benzene with olefins," Sidorov et al., Sernaya Kislota Protsessakh Neftekhim, 172-177, 1975 (Abstract Only).
"High-Temperature Alkylation of Aromatic Hydrocarbons," Sachanen et al., Ind. Eng. Chem. vol. 33, No. 12, pp. 1540-1544 (1941).
"A Kinetic Study on the Homogeneous Liquid-phase Oxidation of Cumene in the Presence of Triphenylsulfonium Chloride," Ohkubo et al., Bull.Chem. Soc. of Japan, vol. 42, No. 7, pp. 1800-1806 (1969).
"Catalytic properties of palladium-zeolite systems in the synthesis of sec-butylbenzene from benzene and ethylene," Isakov et al., Inst. Org. Khim, im. N. D. Zelinskogo, Moscow, Russia, Neftekhimiya (1994), 34(2), 151-70 (Abstract Only; XP002317126).
"Alkylation of benzene by ethylene on catalysts produced from synthetic zeolites ultrasil," Minachev et al., Inst. Org. Khim, im. Zelinskogo, Moscow, USSR, Neftekhimiya (1988), 28(2), 151-8 (Abstract Only: XP-002317128).

(Continued)

*Primary Examiner*—Sikarl A Witherspoon

(57) ABSTRACT

A process for producing phenol and methyl ethyl ketone comprises contacting benzene with a $C_4$ alkylating agent under alkylation conditions with catalyst comprising zeolite beta or a molecular sieve having an X-ray diffraction pattern including d-spacing maxima at 12.4±0.25, 6.9±0.15, 3.57±0.07 and 3.42±0.07 Angstrom to produce an alkylation effluent comprising sec-butylbenzene. The sec-butylbenzene is then oxidized to produce a hydroperoxide and the hydroperoxide is decomposed to produce phenol and methyl ethyl ketone.

41 Claims, 2 Drawing Sheets

OTHER PUBLICATIONS

"Bifunctional catalysts for the alkylation of aromatic compounds by ethylene," Minachev et al., USSR, Lektsii-Vses, Shk. Katal, (1981), vol. 2, 76-111 (Abstract Only: XP-002317129).

"Study of the nature of bifunctional catalysts for the synthesis of sec-butylbenzene from ethylene and benzene," Minachev et al., Inst. Org. Khim, im. Zelinskogo, Moscow, USSR, Geterog. Katal. (1979), 4th, Pt. 2, 485-92 (Abstract Only).

"Study of polyfunctional zeolite catalysts. Communication 2. Formation of a catalyst for synthesis off sec-butylbenzene prepared from nickel acetylacetonate and CaY zeolite," Isakov et al., Inst. Org. Khim. im. Zelinskogo, Moscow, USSR, Izv. Akad Nauk SSSR, Ser. Khim. (1976), (3), 498-504 (Abstract Only).

"Phenol," Process Economics Program Report No. 22B, pp. 113-124, 261 and 263, published by the Stanford Research Institute in Dec. 1977.

* cited by examiner

PROCESS FOR PRODUCING PHENOL AND METHYL ETHYL KETONE

CROSS REFERENCE TO RELATED APPLICATIONS

This application is a 371 National Stage Application of International Application No. PCT/EP2005/008557, filed Aug. 5, 2005, which claims the benefit of Provisional Application No. 60/601,661, filed Aug. 13, 2004, the disclosures of which are herein incorporated by reference.

FIELD OF THE INVENTION

The present invention relates to a process for co-producing phenol and methyl ethyl ketone.

BACKGROUND OF THE INVENTION

Phenol and methyl ethyl ketone are important products in the chemical industry. For example, phenol is useful in the production of phenolic resins, bisphenol A, ε-caprolactam, adipic acid, alkyl phenols, and plasticizers, whereas methyl ethyl ketone can be used as a lacquer, a solvent and for dewaxing of lubricating oils.

The most common route for the production of methyl ethyl ketone is by dehydrogenation of sec-butyl alcohol (SBA), with the alcohol being produced by the acid-catalyzed hydration of butenes. Commercial scale SBA manufacture by butylene with sulfuric acid has be accomplished for many years via gas/liquid extraction. Improvements to this hydration process include a process configuration that utilizes a unique combination of plug flow, bubble column, and CSTR (Stirred Tank Reactor) reaction sections to achieve high conversion of butylene. Other improved processes use spargers, custom-designed for butylene/sulfuric acid absorption/extraction. Also, loop reactors may be preferred to improve mixing intensity. In sec-butyl alcohol dehydrogenation, crude sec-butyl alcohol is recovered in absorption or extraction sections using several towers, preferably, a single tower, to separate sec-butyl alcohol from sec-butyl ether.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that for butenes is likely to increase, due to a developing shortage of propylene. Thus, a process that uses butenes instead of propylene as feed and coproduces methyl ethyl ketone rather than acetone may be an attractive alternative route to the production of phenol.

It is known that phenol and methyl ethyl ketone can be produced by a variation of the Hock process in which sec-butylbenzene is oxidized to obtain sec-butylbenzene hydroperoxide and the peroxide decomposed to the desired phenol and methyl ethyl ketone. An overview of such a process is described in pages 113-421 and 261-263 of Process Economics Report no. 23B entitled "Phenol", published by the Stanford Research Institute in December 1977.

In addition, U.S. Pat. No. 5,298,667 discloses a process for producing phenol and methyl ethyl ketone which comprises the steps of oxidizing sec-butylbenzene to obtain a reaction liquid containing sec-butylbenzene hydroperoxide as the main product, concentrating the reaction liquid by means of a distillation column to obtain a bottom liquid containing sec-butylbenzene hydroperoxide as the main component from the column bottom and decomposing the bottom liquid to obtain phenol and methyl ethyl ketone. The process requires that the sec-butylbenzene starting material is substantially free from (a) ethyl hydroperoxide, carboxylic acids and phenol, (b) styrenes or (c) methylbenzyl alcohol. However, the method used to obtain the required sec-butylbenzene is not disclosed.

European Published Application No. 1,088,809 discloses a process for producing phenol, methyl ethyl ketone and acetone by the oxidation of a mixture containing cumene and up to 25 wt % sec-butylbenzene and the subsequent Hock cleavage of the hydroperoxides, so that the ratio of the phenol:acetone:methyl ethyl ketone in the product can be controlled via the composition of the feed mixture. The feed mixture is produced directly by the alkylation of benzene with a corresponding mixture of propene and 1-butene/2-butene in the presence of a commercial alkylation catalyst such as $AlCl_3$, $H_3PO_4/SiO_2$ or a zeolite.

However, existing commercial catalysts for the alkylation of benzene with butenes, typically $AlCl_3$ and solid phosphoric acid, produce not only sec-butylbenzene but also varying amounts of by-products, mainly isobutylbenzene, tert-butylbenzene, dibutylbenzenes and tributylbenzenes. Of these compounds, dibutylbenzenes and tributylbenzenes are readily separated from the reaction mixture and can then transalkylated to produce additional sec-butylbenzene. However, the boiling points of isobutylbenzene, sec-butylbenzene and tert-butylbenzene are 172.8° C., 173.5° C. and 169° C., respectively, and hence it is difficult to separate these compounds from each other by distillation. Moreover, isobutylbenzene and tert-butylbenzene are known to be inhibitors to the oxidation of sec-butylbenzene to the corresponding hydroperoxide. For example, the rate of oxidation of sec-butylbenzene, when the sec-butylbenzene contains 1% by weight of isobutylbenzene, decreases to about 91% of that when the sec-butylbenzene is free of isobutylbenzene. Similarly, when the isobutylbenzene content is 1.65% by weight, the rate of oxidation decreases to about 86%; when the isobutylbenzene content is 2% by weight, the rate of oxidation decreases to about 84%; and when the isobutylbenzene content is 3.5% by weight, the rate of oxidation decreases to as much as about 82%.

Therefore, in employing the Hock process to coproduce phenol and methyl ethyl ketone, it is important to minimize the amounts of isobutylbenzene and tert-butylbenzene formed as by-products during the alkylation step to produce the sec-butylbenzene.

U.S. Pat. No. 5,059,736 describes a process for producing sec-butylbenzene from benzene and n-butene, comprising reacting benzene and n-butene in the presence of a homogeneous liquid aluminum chloride complex catalyst, said catalyst comprising aluminum chloride, hydrogen chloride, and an aromatic hydrocarbon, wherein the amount of aluminum chloride used as a component of the complex catalyst is from 0.51 to 5% by weight of the benzene used, the reaction temperature is from 20° C. to 70° C., and the amount of isobutylbenzene formed as a by-product is such that the weight ratio of isobutylbenzene to sec-butylbenzene formed is not more than 0.01:1. However, as discussed above, even isobutylbenzene impurities of 1 wt % significantly inhibit the oxidation of sec-butylbenzene to the corresponding hydroperoxide.

It is known from, for example, U.S. Pat. No. 4,992,606 that the synthetic porous crystalline material known as MCM-22 is an effective catalyst for alkylation of aromatic compounds, such as benzene, with alkylating agents, such as olefins, having from 1 to 5 carbon atoms. Similar disclosures are contained in U.S. Pat. Nos. 5,371,310 and 5,557,024 but where the synthetic porous crystalline material is MCM-49 and MCM-56 respectively. However, there is no disclosure or suggestion in these references that MCM-22, MCM-49 or MCM-56 should be unusually selective to sec-butylbenzene when used to catalyze the alkylation of benzene with a $C_4$ alkylating agent.

U.S. Pat. No. 4,891,458 discloses a process for the alkylation or transalkylation of an aromatic hydrocarbon, such as benzene, which comprises contacting the aromatic hydrocarbon with a $C_2$ to $C_4$ olefin alkylating agent or a polyalkyl aromatic hydrocarbon transalkylating agent, under at least partial liquid phase conditions, and in the presence of a catalyst comprising zeolite beta. Suitable olefin alkylating agents are said to include ethylene, propylene, butene-1, trans-butene-2 and cis-butene-2, or mixtures thereof, although the preferred olefins are ethylene and propylene. In the case of the reaction of benzene with n-butenes or polybutylbenzenes, the reaction product is said to include sec-butylbenzene but there is no disclosure as to the level of isobutyl benzene or tert-butyl benzene impurities.

According to the present invention, it has been found that the use of zeolite beta or an MCM-22 family zeolite as the catalyst in the alkylation of benzene with linear butenes produces sec-butylbenzene that is substantially free of isobutylbenzene and tert-butylbenzene and hence is an attractive feed for the Hock cleavage to produce phenol and methyl ethyl ketone.

SUMMARY OF THE INVENTION

In one aspect, the present invention resides in a process for producing phenol and methyl ethyl ketone, the process comprising:

(a) contacting a feed comprising benzene and a $C_4$ alkylating agent under alkylation conditions with catalyst comprising zeolite beta or a molecular sieve having an X-ray diffraction pattern including d-spacing maxima at 12.4±0.25, 6.9±0.15, 3.57±0.07 and 3.42±0.07 Angstrom to produce an alkylation effluent comprising sec-butylbenzene;

(b) oxidizing the sec-butylbenzene from (a) to produce a hydroperoxide; and (c) cleaving the hydroperoxide from (b) to produce phenol and methyl ethyl ketone.

Advantageously, the catalyst used in step (a) is a molecular sieve having an X-ray diffraction pattern including d-spacing maxima at 12.4±0.25, 6.9±0.15, 3.57±0.07 and 3.42±0.07 Angstrom. Conveniently, said sec-butylbenzene contains less than 0.5 wt %, for example less than 0.1 wt %, such as less than 0.05 wt %, of isobutylbenzene.

Conveniently, the $C_4$ alkylating agent in (a) comprises a linear butene, for example 1-butene and/or 2-butene. In one embodiment, said linear butene is contained in a mixed $C_4$ stream which is subjected to at least one of sulfur removal, nitrogen removal, oxygenate removal, butadiene removal and isobutene removal prior to the contacting (a).

Conveniently, the molecular sieve is selected from MCM-22, PSH-3, SSZ-25, ERB-1, ITQ-1, ITQ-2, MCM-36, MCM-49, MCM-56, UZM-8, and mixtures thereof. "Mixtures" as used here and throughout this specification and the appendant claims means any two or more items from the relevant list.

In one embodiment, said contacting (a) is conducted under at least partial liquid phase conditions. Conveniently, said alkylation conditions include a temperature of from about 60° C. to about 260° C., a pressure of 7000 kPa or less, and a feed weight hourly space velocity (WHSV) based on $C_4$ alkylating agent of from about 0.1 to 50 $hr^{-1}$ and a molar ratio of benzene to $C_4$ alkylating agent from about 1 to 50.

In one embodiment, said alkylation effluent produced in (a) comprises polybutylbenzenes and the process further comprises contacting said polybutylbenzenes with benzene in the presence of a transalkylation catalyst to produce sec-butylbenzene. Conveniently, the transalkylation catalyst comprises a molecular sieve selected from zeolite beta, mordenite, USY, MCM-22, PSH-3, SSZ-25, ERB-1, ITQ-1, ITQ-2, MCM-36, MCM-49, MCM-56, UZM-8, and mixtures thereof.

Conveniently, the oxidizing (b) is conducted in the presence of a catalyst, such as a catalyst selected from (i) an oxo (hydroxo) bridged tetranuclear metal complex comprising manganese, (ii) an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from Zn, Fe, Mn, Ga, Al and mixtures thereof and (iii) an N-hydroxy substituted cyclic imide either alone or in the presence of a free radical initiator. In one embodiment, the oxidization catalyst is a heterogeneous catalyst.

Conveniently, the oxidizing (b) is conducted at a temperature of about 70° C. to about 200° C. and a pressure of about 0.5 to about 10 atmospheres (50 to 1000 kPa).

Conveniently, the cleaving (c) is conducted in the presence of a catalyst. The catalyst can be a homogeneous or heterogeneous catalyst. In one embodiment, the catalyst is a homogeneous catalyst, such as sulfuric acid.

Conveniently, the cleaving (c) is conducted at a temperature of about 40° C. to about 120° C., a pressure of about 100 to about 2500 kPa, and a liquid hourly space velocity (LHSV) based on the hydroperoxide of about 0.1 to about 100 $hr^{-1}$.

In further aspect, the present invention resides in a process for producing phenol and methyl ethyl ketone, the process comprising:

(a) contacting benzene with a $C_4$ alkylating agent under alkylation conditions with catalyst to produce an alkylation effluent comprising sec-butylbenzene;

(b) oxidizing the sec-butylbenzene from (a) in the presence of a catalyst to produce a hydroperoxide; and (c) cleaving the hydroperoxide from (b) in the presence of a catalyst to produce a phenol and methyl ethyl ketone, wherein each of the catalysts employed in (a), (b) and (c) is a heterogeneous catalyst.

Conveniently, at least one of, and preferably each of, the contacting (a), oxidizing (b) and cleaving (c) is effected by catalytic distillation.

In yet a further aspect, the invention resides in a process for producing sec-butylbenzene, the process comprising contacting benzene with a $C_4$ alkylating agent under alkylation conditions with catalyst comprising a molecular sieve having an X-ray diffraction pattern including d-spacing maxima at 12.4±0.25, 6.9±0.15, 3.57±0.07 and 3.42±0.07 Angstrom to produce an alkylation effluent comprising sec-butylbenzene containing less than 0.12 wt % of isobutylbenzene or tert-butylbenzene.

DETAILED DESCRIPTION OF THE EMBODIMENTS

Figure 1:
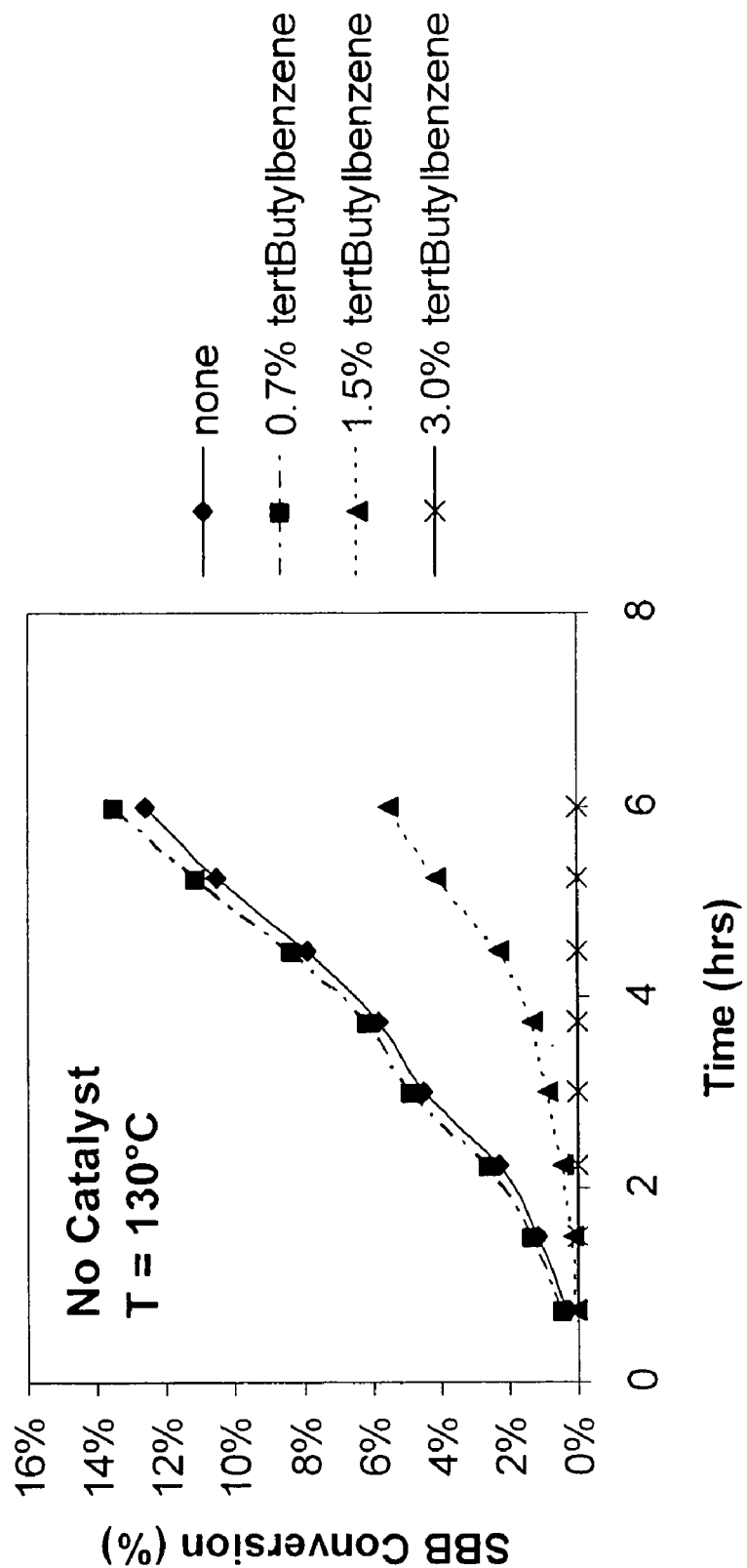
FIG. 1 is a plot of sec-butylbenzene oxidation versus time, for sec-butylbene and sec-butylbenzene/tert-butylbenzene mixtures.

The present invention is directed to a process for producing sec-butylbenzene and then converting the sec-butylbenzene to phenol and methyl ethyl ketone. The conversion involves initially oxidizing the sec-butylbenzene to produce the corresponding hydroperoxide and then cleaving the resulting hydroperoxide to produce the desired phenol and methyl ethyl ketone.

In particular, the invention is based on the discovery that when benzene is alkylated with a $C_4$ alkylating agent, such as a linear butene, over a particular class of heterogeneous, molecular sieve catalysts the alkylation can be controlled to produce sec-butylbenzene that contains less than 0.5 wt %, such as less than 0.1 wt %, of isobutylbenzene and/or tert-butylbenzene which would otherwise act as inhibitors in the oxidation step.

The heterogeneous catalyst in the alkylation step is selected from zeolite beta or a molecular sieve having an X-ray diffraction pattern including d-spacing maxima at 12.4±0.25, 6.9±0.15, 3.57±0.07 and 3.42±0.07 Angstrom. In addition, heterogeneous catalysts are preferably employed in one, or more preferably both, of the oxidation and cleavage steps of the present process.

Benzene Alkylation

The benzene employed in the alkylation step to produce sec-butylbenzene can be any commercially available benzene feed, but preferably the benzene has a purity level of at least 99 wt %.

The alkylating agent can be any aliphatic or aromatic organic compound having one or more available alkylating aliphatic groups capable of reaction with benzene and having 4 carbon atoms. Examples of suitable $C_4$ alkylating agents include monoolefins, such as linear butenes, particularly butene-1 and/or butene-2 and preferably butene-2; alcohols (inclusive of monoalcohols, dialcohols, trialcohols, etc.) such as the butanols; dialkyl ethers, such as dibutyl ethers; and alkyl halides such as the butyl chlorides.

The alkylating agent can also be an olefinic $C_4$ hydrocarbon mixture such as can be obtained by steam cracking of ethane, propane, butane, LPG and light naphthas, catalytic cracking of naphthas and other refinery feedstocks and by conversion of oxygenates, such as methanol, to lower olefins.

For example, the following $C_4$ hydrocarbon mixtures are generally available in any refinery employing steam cracking to produce olefins; a crude steam cracked butene stream, Raffinate-1 (the product of remaining after solvent extraction or hydrogenation to remove butadiene from the crude steam cracked butene stream) and Raffinate-2 (the product remaining after removal of butadiene and isobutene from the crude steam cracked butene stream). Generally, these streams have compositions within the weight ranges indicated in Table 1 below.

TABLE 1

| Component | Crude $C_4$ stream | Raffinate 1 Solvent Extraction | Raffinate 1 Hydrogn. | Raffinate 2 Solvent Extraction | Raffinate 2 Hydrogn. |
|---|---|---|---|---|---|
| Butadiene | 30-85% | 0-2% | 0-2% | 0-1% | 0-1% |
| C4 acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Iso-butane | 0-1% | 0-1% | 0-1% | 0-2% | 0-2% |

Other refinery mixed $C_4$ streams, such as those obtained by catalytic cracking of naphthas and other refinery feedstocks, typically have the following composition:

| | |
|---|---|
| Propylene | 0-2 wt % |
| Propane | 0-2 wt % |
| Butadiene | 0-5 wt % |
| Butene-1 | 5-20 wt % |
| Butene-2 | 10-50 wt % |
| Isobutene | 5-25 wt % |
| Iso-butane | 10-45 wt % |
| N-butane | 5-25 wt % |

$C_4$ hydrocarbon fractions obtained from the conversion of oxygenates, such as methanol, to lower olefins more typically have the following composition:

| | |
|---|---|
| Propylene | 0-1 wt % |
| Propane | 0-0.5 wt % |
| Butadiene | 0-1 wt % |
| Butene-1 | 10-40 wt % |
| Butene-2 | 50-85 wt % |
| Isobutene | 0-10 wt % |
| N- + iso-butane | 0-10 wt % |

Any one or any mixture of the above $C_4$ hydrocarbon mixtures can be used in the process of the invention. In addition to linear butenes and butanes, these mixtures typically contain components, such as isobutene and butadiene, which can be deleterious to the process of the invention. For example, the normal alkylation product of isobutene with benzene is tert-butylbenzene which, as previously stated, acts as an inhibitor to the subsequent oxidation step. Thus, prior to the alkylation step, these mixtures preferably are subjected to butadiene removal and isobutene removal. For example, isobutene can be removed by selective dimerization or reaction with methanol to produce MTBE, whereas butadiene can be removed by extraction or selective hydrogenation to butene-1.

In addition to other hydrocarbon components, commercial $C_4$ hydrocarbon mixtures typically contain other impurities which could be detrimental to the alkylation process. For example, refinery $C_4$ hydrocarbon streams typically contain nitrogen and sulfur impurities, whereas $C_4$ hydrocarbon streams obtained by oxygenate conversion process typically contain unreacted oxygenates and water. Thus, prior to the alkylation step, these mixtures may also be subjected to one or more of sulfur removal, nitrogen removal and oxygenate removal, in addition to butadiene removal and isobutene removal. Removal of sulfur, nitrogen, oxygenate impurities is conveniently effected by one or a combination of caustic treatment, water washing, distillation, adsorption using molecular sieves and/or membrane separation. Water is also typically removed by adsorption.

Although not preferred, it is also possible to employ as the alkylating agent in the alkylation step of the invention a mixture of a $C_4$ alkylating agent, as described above, and $C_3$ alkylating agent, such as propylene, so that the alkylation step produces a mixture of cumene and sec-butylbenzene. The resultant mixture can then be processed through oxidation and cleavage, to make a mixture of acetone and MEK, along with phenol, preferably where the molar ratio of acetone to phenol is 0.5:1, to match the demand of bisphenol-A production.

Conveniently, the total feed to the alkylation step of the present invention contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

As to the molar ratio of benzene to alkylating agent, it is preferable of from 2:1 to 3.5:1, most preferably of from 2.5:1 to 3.2:1.

The alkylation catalyst used in the present process is a crystalline molecular sieve selected from (a) zeolite beta or (b) a material having an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system.

Zeolite beta and its synthesis are disclosed in, for example, U.S. Pat. No. 3,308,069. Materials (b) having said X-ray diffraction pattern are sometimes referred to a molecular sieves of the MCM-22 family and include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

The alkylation catalyst can include the molecular sieve in unbound or self-bound form or, alternatively, the molecular sieve can be combined in a conventional manner with an oxide binder, such as alumina, such that the final alkylation catalyst contains between 2 and 80 wt % sieve.

The alkylation process is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition or in a catalytic distillation reactor, under effective alkylation conditions. Such conditions include a temperature of from about 60° C. to about 260° C., for example between about 100° C. and about 200° C., a pressure of 7000 kPa or less, for example from about 1000 to about 3500 kPa, and a weight hourly space velocity (WHSV) based on $C_4$ alkylating agent of between about 0.1 and about 50 $hr^{-1}$, for example between about 1 and about 10 $hr^{-1}$. Typically, the molar ratio of benzene to alkylating agent is from about 1 to about 50, for example from about 2 to about 10.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen or nitrogen.

Using the catalysts described above, it is found that the alkylation step of the process of the invention is highly selective to sec-butylbenzene. In particular, it is found that the sec-butylbenzene produced normally contains less than 0.5 wt %, for example, less than 0.1 wt %, such as less than 0.05 wt %, of isobutylbenzene or tert-butylbenzene. This is very advantageous, because oxidation of sec-butylbenzene is affected by the presence of iso-butylbenzene and ter-butylbenzene: a significant reduction of sec-butylbenzene occurs when these impurities exceed 0.7 wt % of the sec-butylbenzene feed.

Although the alkylation step is highly selective towards sec-butylbenzene, the effluent from the alkylation reaction will normally contain some polyalkylated oligomerization products, as well as unreacted aromatic feed and the desired monoalkylated species. The unreacted aromatic feed is normally recovered by distillation and recycled to the alkylation reactor. The bottoms from the benzene distillation are further distilled to separate monoalkylated product from any polyalkylated oligomerization products and other heavies. Depending on the amount of polyalkylated oligomerization products present in the alkylation reaction effluent, it may be desirable to transalkylate the polyalkylated oligomerization products with additional benzene to maximize the production of the desired monoalkylated species.

Transalkylation with additional benzene is typically effected in a transalkylation reactor, separate from the alkylation reactor, over a suitable transalkylation catalyst, such as an MCM-22 family catalyst, zeolite beta, MCM-68 (see U.S. Pat. No. 6,014,018), zeolite Y and mordenite. The transalkylation reaction is typically conducted under at least partial liquid phase conditions, which suitably include a temperature of 100 to 300° C., a pressure of 1000 to 7000 kPa, a weight hourly space velocity of 1 to 50 $hr^{-1}$ on total feed, and a benzene/polyalkylated benzene weight ratio of 1 to 10.

When the polyalkylated aromatics are polyethylbenzenes and are reacted with benzene to produce ethylbenzene, the transalkylation conditions preferably include a temperature of 220 to 260° C., a pressure of 2000 to 3000 kPa, a weight hourly space velocity of 2 to 6 on total feed and benzene/PEB weight ratio of 1:1 to 6:1.

Sec-Butyl Benzene Oxidation

The second step in the present process involves oxidation of sec-butylbenzene to the corresponding hydroperoxide and is accomplished by introducing an oxygen-containing gas, such as air, into a liquid phase containing the sec-butylbenzene. The reaction can be performed in the absence of a catalyst but is slow (of the order of <1%/hour at 100 psig (698.5 kPag) pressure). Improvement in the reaction rate can be achieved by performing the oxidation in the presence of a catalyst, such as a water-soluble chelate compound in which multidentate ligands are coordinated to at least one metal from cobalt, nickel, manganese, copper, and iron. (See U.S. Pat. No. 4,013,725). More preferably, a heterogeneous catalyst is used. Suitable heterogeneous catalysts are described in U.S. Pat. No. 5,183,945, wherein the catalyst is an oxo (hydroxo) bridged tetranuclear manganese complex and in U.S. Pat. No. 5,922,920, wherein the catalyst comprises an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from Zn, Fe, Mn, Ga, Al and mixtures thereof. The entire disclosures of said U.S. patents are incorporated herein by reference.

Other suitable catalysts for the sec-butylbenzene oxidation step are the N-hydroxy substituted cyclic imides described in Published U.S. Patent Application No. 2003/0083527 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, 1-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. These materials can be used either alone or in the presence of a free radical initiator and can be used as liquid-phase, homogeneous catalysts or can be supported on a solid carrier to provide a heterogeneous catalyst.

Suitable conditions for the sec-butylbenzene oxidation step include a temperature between about 70° C. and about 200° C., such as about 90° C. to about 130° C., and a pressure of about 0.5 to about 10 atmospheres (50 to 1000 kPa). A basic buffering agent may be added to react with acidic by-products that may form during the oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction is conveniently conducted in a catalytic distillation unit and the sec-butylbenzene hydroperoxide produced may be concentrated by distilling off the unreacted sec-butylbenzene prior to the cleavage step.

Hydroperoxide Cleavage

The third step in the present process involves cleavage of the sec-butylbenzene hydroperoxide to produce the desired phenol and methyl ethyl ketone. The cleavage reaction is effected by contacting the sec-butylbenzene hydroperoxide with a catalyst in the liquid phase at a temperature of about 20° C. to about 150° C., such as about 40° C. to about 120° C., a pressure of about 50 to about 2500 kPa, such as about 100 to about 1000 kPa and a liquid hourly space velocity (LHSV) based on the hydroperoxide of about 0.1 to about 100 hr$^{-1}$, preferably about 1 to about 50 hr$^{-1}$. The sec-butylbenzene hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid A suitable heterogeneous catalyst for use in the cleavage of sec-butylbenzene hydroperoxide includes a smectite clay, such as an acidic montmorillonite silica-alumina clay, as described in U.S. Pat. No. 4,870,217, the entire disclosure of which is incorporated herein by reference.

The following examples are given for illustrative purposes and do not limit the scope of the invention:

EXAMPLE 1

Sec-Butylbenzene Synthesis Using MCM-22

A 0.5 gram sample of an MCM-22 catalyst (65 wt % MCM-22/35% alumina binder) was used for the alkylation of benzene with butene-2. The catalyst was in the form of a 1.6 mm (1/16") diameter cylindrical extrudate and was diluted with sand to 3 cc and loaded into an isothermal, down-flow, fixed-bed, tubular reactor having an outside diameter of 4.76 mm (3/16"). The catalyst was dried at 125° C. and 1 atm with 100 cc/min flowing nitrogen for 2 hours. The nitrogen was turned off and benzene was fed to the reactor at 60 cc/hr for 1 hour and then reduced to desired WHSV while the reactor pressure was increased to 300 psig (2170 kPa). 2-butene (mixture of cis and trans) was introduced from a syringe pump at a 3:1 benzene/butene molar ratio and the reactor temperature was ramped to 160° C. at 5° C./min. Liquid product was collected in a cold-trap and analyzed off line. Butene conversion was determined by measuring unreacted butene relative to feed butene. Stable operation with 95%+ butene conversion was obtained at butene flow rate of 1.5 WHSV. Catalyst performance at 10 and 13 days on stream are shown in Table 2.

EXAMPLE 2

Sec-Butylbenzene Synthesis Using Zeolite Beta

The process of Example 1 was repeated but with the MCM-22 catalyst being replaced by 0.5 gm of a zeolite beta catalyst (65 wt % beta/35% alumina binder), again with the catalyst being in the form of a 1.6 mm (1/16") diameter cylindrical extrudate. Catalyst performance at 1, 3 and 5 days on stream are shown in Table 2.

TABLE 2

| | Catalyst | | | | |
| --- | --- | --- | --- | --- | --- |
| | MCM-22 | | Zeolite Beta | | |
| Days on Stream | 10 | 13 | 1 | 3 | 5 |
| Butene WHSV, h$^{-1}$ | 1.5 | 1.5 | 2.0 | 2.0 | 2.0 |
| 2-Butene Conv, % | 95.8 | 96.4 | 97.5 | 70.4 | 48.5 |
| Product Selectivity, wt % | | | | | |
| iso- & 1-Butene | 0.049 | 0.015 | 0.008 | 3.353 | 6.276 |
| C$_5$-C$_7$ | 0.077 | 0.064 | 0.041 | 0.362 | 0.345 |
| C$_8$ and C$_{12}$ (butene oligomers) | 2.199 | 2.246 | 1.295 | 12.883 | 12.828 |
| Cumene | 0.069 | 0.071 | 0.073 | 0.046 | 0.041 |
| tert-Butylbenzene | 0.099 | 0.098 | 0.623 | 0.112 | 0.108 |
| iso-Butylbenzene* | 0.000 | 0.000 | 0.000 | 0.000 | 0.000 |
| sec-Butylbenzene | 90.911 | 90.812 | 83.237 | 74.931 | 70.144 |
| n-Butylbenzene | 0.013 | 0.013 | 0.020 | 0.005 | 0.007 |
| Di-butylbenzene | 6.064 | 6.105 | 12.664 | 4.330 | 3.355 |
| Tri-butylbenzene | 0.261 | 0.298 | 1.409 | 0.036 | 0.000 |
| Others | 0.258 | 0.276 | 0.630 | 3.942 | 6.895 |
| Sum | 100.00 | 100.00 | 100.00 | 100.00 | 100.00 |
| Butylbenzene Composition, % | | | | | |
| t-Butylbenzene | 0.109 | 0.108 | 0.742 | 0.149 | 0.153 |
| iso-Butylbenzene* | 0.000 | 0.000 | 0.000 | 0.000 | 0.000 |
| sec-Butylbenzene | 99.877 | 99.877 | 99.233 | 99.844 | 99.837 |
| n-Butylbenzene | 0.014 | 0.014 | 0.024 | 0.007 | 0.010 |
| Sum | 100.00 | 100.00 | 100.00 | 100.00 | 100.00 |

*Iso-Butylbenzene not measurable (could be obscured by sec-butylbenzene given close elution times).

Data in Table 2 show that MCM-22 catalyst was highly active and selective for the production of sec-butylbenzene without producing a measurable quantity of iso-butylbenzene and very low quantities of tert-butylbenzene. MCM-22 was also quite stable with no sign of deactivation during the 13-day test cycle. Zeolite beta showed good initial activity. Although it deactivated rapidly as a result of butene oligomer formation, zeolite beta produced sec-butylbenzene without producing measurable quantities of iso-butylbenzene. Zeolite beta produced low quantities of tert-butylbenzene, albeit not as low as MCM-22. When compared at 95+% conversion, MCM-22 was about 8% more selective than zeolite beta for sec-butylbenzene production.

EXAMPLE 3

Sec-Butylbenzene Synthesis Using MCM-22

A 1.0 gram sample of the same MCM-22 catalyst (65% MCM-22/35% alumina binder) as used in Example 1 was used for the alkylation of benzene with 2-butene. The catalyst was in the form of a 1.6 mm (1/16") diameter cylindrical extrudate, chopped to 1/16" length, and was diluted with sand to 3 cc and loaded into an isothermal, down-flow, fixed-bed, tubular reactor having an outside diameter of 4.76 mm (3/16"). The catalyst was dried at 150° C. and 1 atm with 100 cc/min flowing nitrogen for 2 hours. The nitrogen was turned off and benzene was fed to the reactor at 60 cc/hr for 1 hour and then reduced to desired WHSV while the reactor pressure was increased to 300 psig (2170 kPa). Butene feed (57.1% cis-butene, 37.8% trans-butene, 2.5% n-butane, 0.8% isobutene and 1-butene, and 1.8% others) was introduced from a syringe pump at a 3:1 benzene/butene molar ratio, and this ratio was kept constant for the entire run. The reactor temperature was ramped to 160° C. at 2° C./min. Liquid products were collected at reactor conditions of 160° C. and 300 psig in a cold-trap and analyzed off line. 2-Butene conversion was determined by measuring unreacted 2-butene relative to feed 2-butene.

The catalyst was on stream for 4 days at 1.6 WHSV of butene with 97% 2-butene conversion, 2 days at 4.8 WHSV with 95% conversion, then 1 day at 7.2 WHSV with 86% conversion, and followed by 4 days again at 1.6 WHSV with 97% conversion. No deactivation was detected during the 11-day test cycle. Representative data are shown in Table 3.

EXAMPLE 4

Sec-Butylbenzene Synthesis Using Solid Phosphoric Acid (SPA)

The process of Example 3 was repeated but with the MCM-22 catalyst being replaced by 1.6 gm of a solid phosphoric acid (SPA catalyst, commercially available from UOP). The catalyst was sized to 14-24 mesh and loaded to the reactor in a glove bag with nitrogen purge. Representative data are shown in Table 3.

TABLE 3

| | Catalyst | | | | | | |
|---|---|---|---|---|---|---|---|
| | MCM-22 | | | | SPA | | |
| Days on Stream | 3.8 | 5.9 | 7.1 | 10.8 | 0.79 | 1.79 | 2.79 |
| Butene WHSV, $h^{-1}$ | 1.6 | 4.8 | 7.2 | 1.6 | 1.0 | 1.0 | 1.0 |
| 2-Butene Conv, % | 97.7 | 95.3 | 86.0 | 97.2 | 80.0 | 67.9 | 61.3 |
| Product Selectivity, wt % | | | | | | | |
| Iso-Butane | 0.010 | 0.001 | 0.004 | 0.008 | 0.014 | 0.031 | 0.021 |
| Iso-Butene & 1-Butene | 0.000 | 0.020 | 0.355 | 0.000 | 0.965 | 2.482 | 3.970 |
| $C_5$-$C_7$ | 0.227 | 0.105 | 0.132 | 0.120 | 0.214 | 0.306 | 0.215 |
| $C_8$ and $C_{12}$ (butene oligomers) | 0.812 | 1.753 | 2.556 | 1.910 | 6.567 | 8.856 | 8.968 |
| Cumene | 0.077 | 0.050 | 0.031 | 0.059 | 0.052 | 0.045 | 0.047 |
| t-Butylbenzene | 0.158 | 0.060 | 0.026 | 0.103 | 0.933 | 1.090 | 0.946 |
| iso-Butylbenzene* | 0.000 | 0.000 | 0.000 | 0.000 | 0.000 | 0.000 | 0.000 |
| sec-Butylbenzene | 89.185 | 90.983 | 90.490 | 91.553 | 87.755 | 85.087 | 84.205 |
| n-Butylbenzene | 0.024 | 0.031 | 0.030 | 0.025 | 0.019 | 0.021 | 0.023 |
| Di-butylbenzene | 8.012 | 6.589 | 5.982 | 5.791 | 3.109 | 1.938 | 1.507 |
| Tri-butylbenzene | 1.239 | 0.420 | 0.392 | 0.417 | 0.216 | 0.118 | 0.077 |
| Heavies | 0.256 | 0.008 | 0.003 | 0.013 | 0.155 | 0.028 | 0.020 |
| Sum | 100.00 | 100.00 | 100.00 | 100.00 | 100.00 | 100.00 | 100.00 |
| Butylbenzene Composition, % | | | | | | | |
| t-Butylbenzene | 0.177 | 0.065 | 0.029 | 0.112 | 1.052 | 1.265 | 1.110 |
| iso-Butylbenzene* | 0.000 | 0.000 | 0.000 | 0.000 | 0.000 | 0.000 | 0.000 |
| sec-Butylbenzene | 99.796 | 99.900 | 99.938 | 99.860 | 98.926 | 98.711 | 98.863 |
| n-Butylbenzene | 0.027 | 0.034 | 0.033 | 0.028 | 0.021 | 0.025 | 0.027 |
| Sum | 100.00 | 100.00 | 100.00 | 100.00 | 100.00 | 100.00 | 100.00 |

*Iso-Butylbenzene not measurable (could be obscured by sec-butylbenzene given close elution times).

Data in Table 3 show that the MCM-22 catalyst was much more active, selective, and stable than the SPA catalyst. When compared at 80-86% conversion, MCM-22 is at least 7-times more active than the SPA. MCM-22 is also highly selective for sec-butylbenzene production with much lower tendency than SPA to form butene oligomers. MCM-22 was stable during the 11-day test cycle without any indication of deactivation. Sec-butylbenzene purity is also superior with the MCM-22 catalyst. SPA was active for this reaction but deactivated rapidly with time on stream. Its overall performance was poor compared to the performance of MCM-22.

EXAMPLE 5

Sec-Butylbenzene Synthesis Using MCM-49

The process of Example 3 was repeated but with the MCM-22 catalyst replaced by a) 0.5 gm of MCM-49-A, b) 0.6 gm of MCM-49-B, and c) 0.5 gm of MCM-49-C. The catalyst information and experimental sequence for each run are provided below:

aggregated zeolite crystal by rubbing and colliding them each other through blowing high-speed jet stream emitted from several pieces of grinding nozzles into the material layer in the grinding chamber). The catalyst was on stream for 5 days at 3.2 WHSV of butene with 98% 2-butene conversion, 1.1 days at 9.6 WHSV with 97% conversion, 4 day at 3.2 WHSV with 98% conversion, 0.4 days at 23 WHSV with 89% conversion, and followed by 3 days at 3.2 WHSV again with 98% conversion.

Representative data are shown in Table 4. The data in Table 4 shows that MCM-49 catalysts are much more active, selective and stable than solid phosphoric acid in catalyzing the formation of sec-butylbenzene from benzene and ethylene.

TABLE 4

| | Catalyst | | | | | |
|---|---|---|---|---|---|---|
| | MCM-49-A | MCM-49-B | MCM-49-C | MCM-49-A | MCM-49-B | MCM-49-C |
| Days on Stream | 9.8 | 4.7 | 5.9 | 7.1 | 7.1 | 10.1 |
| Butene WHSV, $h^{-1}$ | 3.2 | 8.0 | 9.6 | 14.4 | 19.2 | 23.1 |
| 2-Butene Conv, % | 94.1 | 96.7 | 97.4 | 84.0 | 86.3 | 89.2 |
| Product Selectivity, wt % | | | | | | |
| Iso-Butane | 0.012 | 0.004 | 0.005 | 0.003 | 0.003 | 0.003 |
| Iso-Butene & 1-Butene | 0.052 | 0.000 | 0.000 | 0.406 | 0.358 | 0.298 |
| $C_5$-$C_7$ | 0.186 | 0.109 | 0.115 | 0.149 | 0.089 | 0.180 |
| $C_8$ and $C_{12}$ (butene oligomers) | 2.043 | 1.428 | 1.768 | 1.632 | 1.852 | 2.133 |
| Cumene | 0.048 | 0.045 | 0.057 | 0.032 | 0.042 | 0.045 |
| t-Butylbenzene | 0.064 | 0.069 | 0.092 | 0.044 | 0.042 | 0.046 |
| iso-Butylbenzene* | 0.000 | 0.000 | 0.000 | 0.000 | 0.000 | 0.000 |
| sec-Butylbenzene | 91.426 | 92.400 | 91.802 | 91.510 | 91.759 | 91.727 |
| n-Butylbenzene | 0.022 | 0.025 | 0.023 | 0.013 | 0.013 | 0.032 |
| Di-butylbenzene | 5.747 | 5.664 | 5.820 | 5.921 | 5.649 | 5.296 |
| Tri-butylbenzene | 0.393 | 0.250 | 0.306 | 0.284 | 0.189 | 0.235 |
| Heavies | 0.008 | 0.006 | 0.012 | 0.006 | 0.006 | 0.006 |
| Sum | 100.0 | 100.0 | 100.0 | 100.0 | 100.0 | 100.0 |
| Butylbenzene Composition, % | | | | | | |
| t-Butylbenzene | 0.070 | 0.075 | 0.100 | 0.048 | 0.046 | 0.050 |
| iso-Butylbenzene* | 0.000 | 0.000 | 0.000 | 0.000 | 0.000 | 0.000 |
| sec-Butylbenzene | 99.907 | 99.898 | 99.875 | 99.938 | 99.940 | 99.916 |
| n-Butylbenzene | 0.024 | 0.027 | 0.025 | 0.014 | 0.014 | 0.034 |
| Sum | 100.0 | 100.0 | 100.0 | 100.0 | 100.0 | 100.0 |

*Iso-Butylbenzene not measurable (could be obscured by sec-butylbenzene given close elution times).

MCM-49-A: 1/20" quadrulobe extrudate with 80% MCM-49/20% alumina binder, cut to 1/20" length. The catalyst was on stream for 6 days at 3.2 WHSV of butene with 96% 2-butene conversion, 0.8 days at 9.6 WHSV with 88% conversion, 0.6 day at 14.4 WHSV with 85% conversion, and followed by 3 days at 3.2 WHSV again with 95% conversion.

MCM-49-B: 1/20" quadrulobe extrudate with 60% MCM-49/40% Versal 200 alumina binder, cut to 1/20" length. The catalyst was on stream for 4 days at 2.7 WHSV of butene with 98% conversion, 1 day at 8 WHSV with 97% conversion, 0.5 days at 12 WHSV with 93% conversion, 1.6 days at 2.7 WHSV with 98% conversion, 0.3 days at 19.2 WHSV with 86% conversion, and followed by 0.7 days at 2.7 WHSV again with 98% conversion.

MCM-49-C: 1/20" quadrulobe extrudate with 80% MCM-49/20% alumina binder, cut to 1/20" length. The MCM-49 crystal was jet-milled prior to extrusion with alumina (Jet Mill grinds

EXAMPLE 6

Sec-Butylbenzene Synthesis Using MCM-22 and Mixed Butene Feed

A 1.0 gram sample of the same MCM-22 catalyst (65% MCM-22/35% alumina binder) as used in Example 1 was used for the alkylation of benzene with a butene feed. The process of Example 3 was repeated but with the feed being replaced by a new feed with the following composition: 53.4% cis-butene, 41.2% trans-butene, 4.6% isobutene, 0.5% butadiene, 0.1% n-butane and 0.2% others.

The catalyst was on stream for 6 days at 1.6 WHSV of butene with 98% 2-butene conversion, 1 day at 4.8 WHSV with 80% conversion, 1 day at 7.2 WHSV with 62% conversion, then followed by 4 days again at 1.6 WHSV with 97% conversion. Representative data are shown in Table 5 below.

TABLE 5

| | Sample # | | | | | | |
|---|---|---|---|---|---|---|---|
| | 1 | 3 | 6 | 8 | 11 | 13 | 15 |
| Days on Stream | 0.79 | 2.79 | 5.79 | 7.33 | 8.19 | 9.8 | 11.79 |
| Butene WHSV, $h^{-1}$ | 1.6 | 1.6 | 1.6 | 4.8 | 7.2 | 1.6 | 1.6 |
| 2-Butene Conv, % | 98.6 | 98.0 | 98.4 | 79.8 | 62.1 | 96.9 | 97.0 |
| Isobutene Conv, % | 98.2 | 96.3 | 96.8 | 64.4 | 35.8 | 93.7 | 94.0 |
| Butadiene Conv, % | 100.0 | 100.0 | 100.0 | 100.0 | 96.4 | 100.0 | 100.0 |
| Product Selectivity, wt % | | | | | | | |
| $i\text{-}C_4$ | 0.047 | 0.039 | 0.034 | 0.023 | 0.025 | 0.027 | 0.025 |
| $C_5\text{-}C_7$ | 0.388 | 0.525 | 0.467 | 0.541 | 0.640 | 0.556 | 0.555 |
| $C_8$ and $C_{12}$ (butene oligomers) | 8.739 | 7.886 | 7.746 | 10.343 | 12.852 | 7.916 | 8.230 |
| Cumene | 0.175 | 0.183 | 0.189 | 0.183 | 0.194 | 0.196 | 0.172 |
| t-Butylbenzene | 2.319 | 1.577 | 1.521 | 0.697 | 0.561 | 1.267 | 1.224 |
| iso-Butylbenzene* | 0.000 | 0.000 | 0.000 | 0.000 | 0.000 | 0.000 | 0.000 |
| sec-Butylbenzene | 81.330 | 83.058 | 83.282 | 82.789 | 81.265 | 83.453 | 83.406 |
| n-Butylbenzene | 0.034 | 0.059 | 0.055 | 0.063 | 0.058 | 0.060 | 0.062 |
| Di-butylbenzene | 5.227 | 5.559 | 5.580 | 4.642 | 3.972 | 5.465 | 5.312 |
| Tri-butylbenzene | 1.456 | 0.887 | 0.926 | 0.495 | 0.378 | 0.837 | 0.840 |
| Heavies | 0.284 | 0.225 | 0.200 | 0.225 | 0.055 | 0.224 | 0.174 |
| Sum | 100.00 | 100.00 | 100.00 | 100.000 | 100.000 | 100.00 | 100.00 |
| Butylbenzene Composition, % | | | | | | | |
| t-Butylbenzene | 2.772 | 1.863 | 1.792 | 0.835 | 0.685 | 1.494 | 1.445 |
| iso-Butylbenzene* | 0.000 | 0.000 | 0.000 | 0.000 | 0.000 | 0.000 | 0.000 |
| sec-Butylbenzene | 97.187 | 97.817 | 98.143 | 99.091 | 99.244 | 98.435 | 98.482 |
| n-Butylbenzene | 0.041 | 0.070 | 0.064 | 0.075 | 0.071 | 0.071 | 0.073 |
| Sum | 100.00 | 100.00 | 100.00 | 100.000 | 100.000 | 100.00 | 100.00 |

*Iso-Butylbenzene not measurable (could be obscured by sec-butylbenzene given close elution times).

Data in Table 5 show that the MCM-22 catalyst was effective for sec-butylbenzene production using a 2-butene feed with 4.6% isobutene and 0.5% butadiene. The presence of 0.5% butadiene caused no significant deactivation of MCM-22 during the 12-day test cycle. The presence of 4.6% isobutene in butene feed resulted less than 2% tert-butylbenzene formation in the combined butylbenzene fraction after initial lineout. The increased butene oligomer formation is caused by increased isobutene which oligomerizes more readily than it undergoes alkylation with benzene.

EXAMPLE 7

Sec-Butylbenzene Synthesis Using MCM-22 and Mixed Butene Feed

The procedure of Example 6 was followed except the MCM-22 catalyst was replaced with 0.5 gm of catalyst MCM-49-B mentioned at Example 5. Catalyst MCM-49-B was on stream for 3 days at 3.2 WHSV of butene with 96% conversion, 0.7 days at 9.6 WHSV with 83% conversion, and followed by 3 days at 3.2 WHSV again with 95% conversion. Representative data is given in Table 6.

TABLE 6

| | Sample # | | |
|---|---|---|---|
| | 2 | 5 | 8 |
| Days on Stream | 2.3 | 3.2 | 5.3 |
| Butene WHSV, $h^{-1}$ | 3.20 | 9.60 | 3.20 |
| 2-Butene Conv, % | 96.1 | 83.0 | 95.5 |
| Isobutene Conv, % | 97.7 | 67.2 | 92.8 |
| Butadiene Conv, % | 100.0 | 100.0 | 100.0 |

TABLE 6-continued

| | Sample # | | |
|---|---|---|---|
| | 2 | 5 | 8 |
| Product Selectivity, wt % | | | |
| $i\text{-}C_4$ | 0.041 | 0.032 | 0.028 |
| $C_5\text{-}C_7$ | 0.527 | 0.503 | 0.583 |
| $C_8$ and $C_{12}$ (butene oligomers) | 7.688 | 9.732 | 8.185 |
| Cumene | 0.128 | 0.144 | 0.127 |
| t-Butylbenzene | 1.849 | 0.849 | 1.240 |
| iso-Butylbenzene* | 0.000 | 0.008 | 0.012 |
| sec-Butylbenzene | 82.977 | 84.284 | 84.720 |
| n-Butylbenzene | 0.062 | 0.059 | 0.068 |
| Di-butylbenzene | 5.431 | 3.878 | 4.273 |
| Tri-butylbenzene | 1.079 | 0.429 | 0.629 |
| Heavies | 0.218 | 0.082 | 0.134 |
| Sum | 100.0 | 100.0 | 100.0 |
| Butylbenzene Composition, % | | | |
| t-Butylbenzene | 2.179 | 0.996 | 1.441 |
| iso-Butylbenzene* | 0.000 | 0.010 | 0.013 |
| sec-Butylbenzene | 97.749 | 98.925 | 98.467 |
| n-Butylbenzene | 0.073 | 0.069 | 0.078 |
| Sum | 100.0 | 100.0 | 100.0 |

*Iso-Butylbenzene not measurable (could be obscured by sec-butylbenzene given close elution times).

EXAMPLE 8

Sec-Butylbenzene Oxidation

To a 250-ml round bottom flask fitted with a condenser, stirrer and an air sparger, was charged 75.0 g of sec-butylbenzene (Aldrich). The flask was heated using a temperature-controlled heating mantle. Reaction temperature was 100° C. Reaction pressure was approximately atmospheric. The air flowrate was approximately 175 cc/min. Every 45 minutes, a small aliquot of the reaction mixture was removed from the flask and analyzed by GC. The rate of oxidation of the sec-butylbenzene in the absence of a catalyst was approximately 0.1% per hour.

EXAMPLE 9

Effect of Impurities on Sec-Butylbenzene Oxidation

Figure 2:
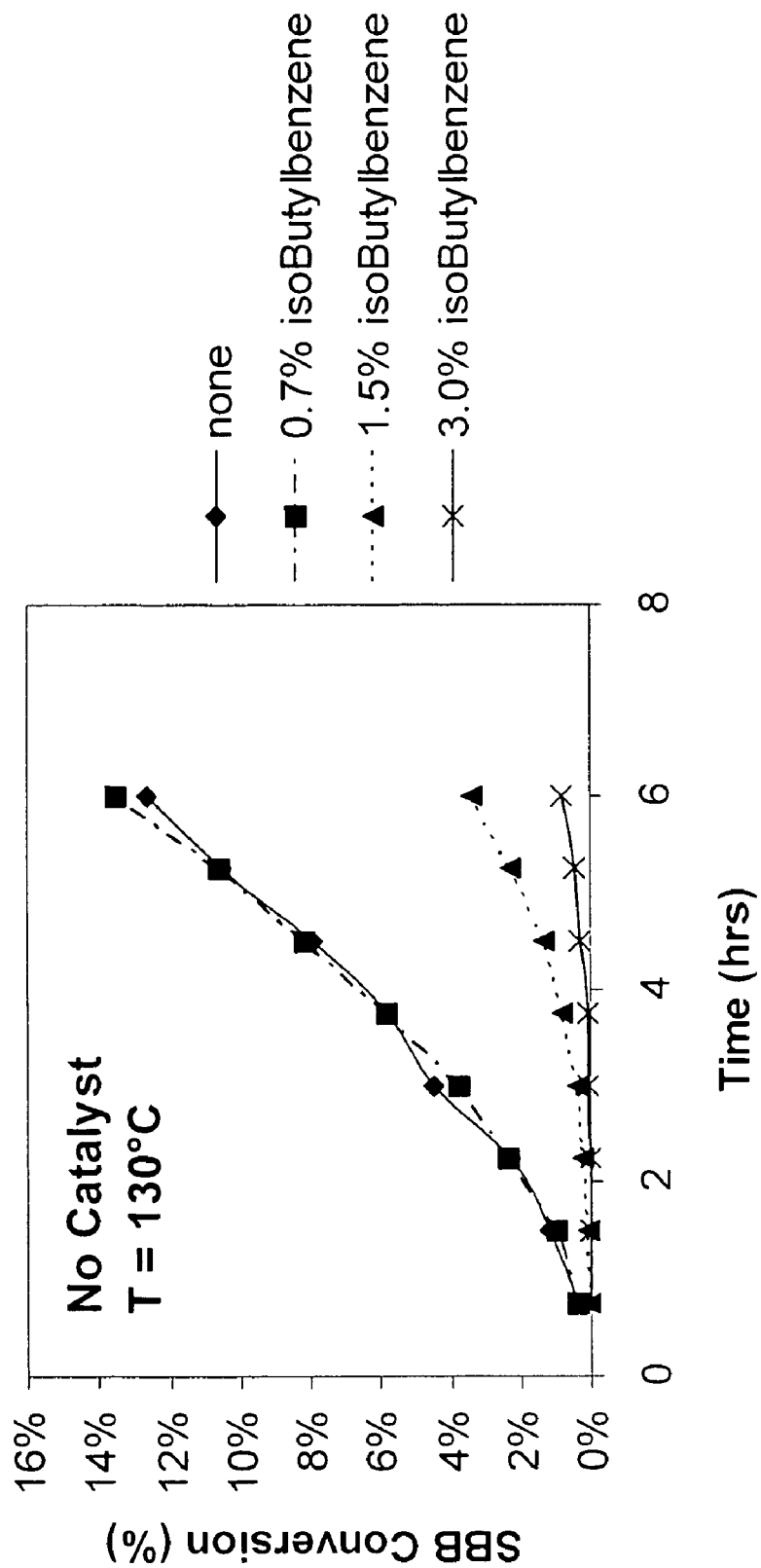
FIG. 2 is a plot of sec-butylbenzene oxidation versus time, for sec-butylbene and sec-butylbenzene/iso-butylbenzene mixtures

The procedure of Example 8 was repeated, except known amounts of iso-butylbenzene and tert-butylbenzene were added to the sec-butylbenzene feedstream. The results are shown in FIGS. 1 and 2, that show that, at concentrations above 0.7 wt %, sec-butylbenzene oxidation is affected by the presence of iso-butylbenzene or tert-butylbenzene.

EXAMPLE 9

Sec-Butylbenzene Oxidation

To a 250-ml round bottom flask fitted with a condenser, stirrer and an air sparger, was charged 75.0 g of sec-butylbenzene (Aldrich) and 0.1 g of a $BaMnO_4$ catalyst produced according to Preparation 1 of U.S. Pat. No. 5,922,920. The flask was heated using a temperature-controlled heating mantle. Reaction temperature was 100° C. Reaction pressure was approximately atmospheric. The air flowrate was approximately 175 cc/min. Every 45 minutes, a small aliquot of the reaction mixture was removed from the flask and analyzed by GC. The rate of oxidation of the sec-butylbenzene in the presence of the $BaMnO_4$ catalyst was 7 times faster than that of the non-catalyzed oxidation of Example 8.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol and methyl ethyl ketone, the process comprising:
    (a) contacting a feed comprising benzene and a C4 alkylating agent under alkylation conditions with catalyst comprising a molecular sieve having an X-ray diffraction pattern including d-spacing maxima at 12.4±0.25, 6.9±0.15, 3.57±0.07 and 3.42±0.07 Angstrom to produce an alkylation effluent comprising sec-butylbenzene wherein said C4 alkylating agent is contained in a $C_4$ hydrocarbon mixture comprising butene-1, isobutene and butadiene and
    wherein, prior to alkylation, the $C_4$ hydrocarbon mixture is subjected to butadiene removal and isobutene removal;
    (b) oxidizing the sec-butylbenzene from (a) to produce a hydroperoxide wherein said oxidizing (b) is conducted in the presence of a catalyst wherein said oxidation catalyst is an N-hydroxy substituted cyclic imide either alone or in the presence of a free radical initiator; and
    c) cleaving the hydroperoxide from (b) to produce phenol and methyl ethyl ketone.

2. A process for producing sec-butylbenzene, the process comprising (a) contacting a feed comprising benzene and a C4 alkylating agent under alkylation conditions with catalyst comprising a molecular sieve having an X-ray diffraction pattern including d-spacing maxima at 12.4±0.25, 6.9±0.15, 3.57±0.07 and 3.42±0.07 Angstrom to produce an alkylation effluent comprising sec-butylbenzene containing less than 0.12 wt % of isobutylbenzene or tert-butylbenzene.

3. The process of claim 1, wherein said sec-butylbenzene contains less than 0.1 wt % of isobutylbenzene.

4. The process of claim 1, wherein said sec-butylbenzene contains less than 0.1 wt % of tert-butylbenzene.

5. The process of claim 1, wherein said sec-butylbenzene contains less than 0.5 wt % of iso- and tert-butylbenzene.

6. The process of claim 1, wherein the isobutene removal can be effected by selective dimerization or reaction with methanol to produce MTBE.

7. The process of claim 1, wherein the isobutene removal can be effected by selective dimerization.

8. The process of claim 1, wherein the butadiene removal can be effected by extraction or selective hydrogenation to butene-1.

9. The process of claim 1, wherein said C4 alkylating agent in contacting step (a) comprises a linear butene and wherein said linear butene is contained in a mixed C4 stream.

10. The process of claim 9, wherein said mixed C4 stream is derived from a steam-cracked crude C4 stream comprising the following major components:

| |
|---|
| 30 to 85 wt % butadiene |
| 0 to 15 wt % C4 acetylenics |
| 1 to 30 wt % butene-1 |
| 1 to 15 wt % butene-2 |
| 0 to 30 wt % isobutene |
| 0 to 10 wt % normal-butane |
| 0 to 1 wt % iso-butane. |

11. The process of claim 9, wherein said mixed C4 stream is derived from a raffinate stream obtained by subjecting a steam-cracked crude C4 stream to a solvent extraction process to remove butadiene, wherein said raffinate stream comprises the following major components:

| |
|---|
| 0 to 2 wt % butadiene |
| 0 to 0.5 wt % C4 acetylenics |
| 20 to 50 wt % butene-1 |
| 10 to 30 wt % butene-2 |
| 0 to 55 wt % isobutene |
| 0 to 55 wt % normal-butane |
| 0 to 1 wt % iso-butane. |

12. The process of claim 9, wherein said mixed C4 stream is derived from a raffinate stream obtained by subjecting a steam-cracked crude C4 stream to a hydrogenation process to remove butadiene, wherein said raffinate stream comprises the following major components:

| |
|---|
| 0 to 2 wt % butadiene |
| 0 to 0.5 wt % C4 acetylenics |
| 50 to 95 wt % butene-1 |
| 0 to 20 wt % butene-2 |
| 0 to 35 wt % isobutene |
| 0 to 10 wt % normal-butane |
| 0 to 1 wt % iso-butane. |

13. The process of claim 9, wherein said mixed C4 stream is derived from a raffinate stream obtained by subjecting a steam-cracked crude C4 stream to a solvent extraction process to remove butadiene and to an iso-butene removal process, wherein said raffinate stream comprises the following major components:

| |
|---|
| 0 to 1 wt % butadiene |
| 0 to 0.5 wt % C4 acetylenics |
| 25 to 75 wt % butene-1 |
| 15 to 40 wt % butene-2 |
| 0 to 5 wt % isobutene |
| 0 to 55 wt % normal-butane |
| 0 to 2 wt % iso-butane. |

14. The process of claim 9, wherein said mixed C4 stream is derived from a raffinate stream obtained by subjecting a steam-cracked crude C4 stream to a hydrogenation process to remove butadiene and to an iso-butene removal process, wherein said raffinate stream comprises the following major components:

| |
|---|
| 0 to 1 wt % butadiene |
| 0 to 0.5 wt % C4 acetylenics |
| 75 to 95 wt % butene-1 |
| 0 to 20 wt % butene-2 |
| 0 to 5 wt % isobutene |
| 0 to 10 wt % normal-butane |
| 0 to 2 wt % iso-butane. |

15. The process of claim 9, wherein said mixed C4 stream is a refinery mixed butane/butene stream.

16. The process of claim 15 wherein said refinery mixed butane/butene stream comprises the following major components:

| |
|---|
| 0 to 2 wt % propylene |
| 0 to 2 wt % propane |
| 0 to 5 wt % butadiene |
| 5 to 20 wt % butene-1 |
| 10 to 50 wt % butene-2 |
| 5 to 25 wt % isobutene |
| 10 to 45 wt % iso-butane |
| 5 to 25 wt % n-butane. |

17. The process of claim 9, wherein said mixed C4 stream is derived from a C4 fraction obtained from an oxygenate to olefin conversion process.

18. The process of claim 17, wherein said C4 fraction comprises the following major components:

| |
|---|
| 0 to 1 wt % propylene |
| 0 to 0.5 wt % propane |
| 0 to 1 wt % butadiene |
| 10 to 40 wt % butene-1 |
| 50 to 85 wt % butene-2 |
| 0 to 10 wt % isobutene |
| 0 to 10 wt % normal and isobutane. |

19. The process of claim 9, wherein said mixed C4 stream is produced by combining a plurality of olefinic C4 hydrocarbons or mixtures thereof.

20. The process of claim 9, wherein said mixed C4 stream is subjected to at least one of sulfur removal, nitrogen removal, oxygenate removal, butadiene removal and isobutene removal prior to the contacting (a).

21. The process of claim 1, wherein the feed in (a) comprises less than 1000 ppm, such as less than 500 ppm, for example less than 100 ppm, water.

22. The process of claim 1, wherein the feed in (a) comprises less than 100 ppm, such as less than 30 ppm, for example less than 3 ppm, sulfur.

23. The process of claim 1, wherein the feed in (a) comprises less than 10 ppm, such as less than 1 ppm, for example less than 0.1 ppm, nitrogen.

24. The process of claim 1, wherein the catalyst in (a) is selected from MCM-22, MCM-49 and mixtures thereof.

25. The process of claim 1 wherein the molecular sieve in (a) is selected from MCM-22, PSH-3, SSZ-25, ERB-1, ITQ-1, ITQ-2, MCM-36, MCM-49, MCM-56, UZM-8, and mixtures thereof.

26. The process of claim 1, wherein said contacting (a) is conducted under at least partial liquid phase conditions.

27. The process of claim 1, wherein said alkylation conditions include a temperature of from about 60° C. to about 260° C., a pressure of 7000 kPa or less, and a feed weight hourly space velocity (WHSV) based on C4 alkylating agent of from about 0.1 to 50 hr$^{-1}$ and a molar ratio of benzene to C4 alkylating agent from about 1 to about 50.

28. The process of claim 1, wherein said alkylation effluent produced in (a) comprises polybutylbenzenes and the process further comprises contacting said polybutylbenzenes with benzene in the presence of a transalkylation catalyst to produce sec-butylbenzene.

29. The process of claim 28, wherein the transalkylation catalyst comprises a molecular sieve selected from zeolite beta, mordenite, USY, MCM-22, PSH-3, SSZ-25, ERB-1, ITQ-1, ITQ-2, MCM-36, MCM-49, MCM-56, UZM-8, and mixtures thereof.

30. The process of claim 1, wherein the oxidizing (b) is conducted at a temperature of about 70° C. to about 200° C. and a pressure of about 0.5 to about 10 atmospheres (50 to 1000 kPa).

31. The process of claim 1, wherein the cleaving (c) is conducted in the presence of a catalyst.

32. The process of claim 31, wherein the cleaving (c) is conducted in the presence of a homogeneous catalyst.

33. The process of claim 32, wherein said homogeneous catalyst comprises at least one of sulfuric acid, perchloric acid, phosphoric acid, hydrochloric acid, p-toluenesulfonic acid, ferric chloride, boron trifluoride, sulfur dioxide and sulfur trioxide.

34. The process of claim 32, wherein said homogeneous catalyst comprises sulfuric acid.

35. The process of claim 31, wherein the cleaving (c) is conducted in the presence of a heterogeneous catalyst.

36. The process of claim 35, wherein said heterogeneous catalyst comprises a smectite clay.

37. The process of claim 1, wherein the cleaving (c) is conducted at a temperature of about 40° C. to about 120(C, a pressure of about 100 to about 1000 kPa, and a liquid hourly space velocity (LHSV) based on the hydroperoxide of about 1 to about 50 hr-1.

38. The process according to claim 1 wherein oxidizing (b) is performed in the presence of a catalyst, and cleaving (c) is performed in the presence of a catalyst, and wherein each of the catalysts employed in (a), (b) and (c) is a heterogeneous catalyst.

39. The process of claim 38, wherein said alkylation effluent produced in (a) comprises polybutylbenzenes and the process further comprises contacting said polybutylbenzenes with benzene in the presence of a heterogeneous transalkylation catalyst to produce sec-butylbenzene.

40. The process of claim 1, wherein at least one of the contacting (a), oxidizing (b) and cleaving (c) is effected by catalytic distillation.

41. The process of claim 1, wherein each of the contacting (a), oxidizing (b) and cleaving (c) is effected by catalytic distillation.

* * * * *